United States Patent
Beheshti et al.

(10) Patent No.: US 8,100,191 B2
(45) Date of Patent: Jan. 24, 2012

(54) VAPOUR EXPLOSION CHAMBER

(75) Inventors: Novid Beheshti, Birmingham (GB); Andrew McIntosh, Leeds (GB)

(73) Assignee: The University of Leeds, Leeds (GB)

( * ) Notice: Subject to any disclaimer, the term of this patent is extended or adjusted under 35 U.S.C. 154(b) by 113 days.

(21) Appl. No.: 11/528,297

(22) Filed: Sep. 26, 2006

(65) Prior Publication Data

US 2011/0062249 A1 Mar. 17, 2011

Related U.S. Application Data

(60) Provisional application No. 60/720,716, filed on Sep. 26, 2005.

(51) Int. Cl.
*A62C 13/62* (2006.01)
*B05B 1/24* (2006.01)

(52) U.S. Cl. ............... 169/68; 169/6; 239/13; 239/337

(58) Field of Classification Search .................. 239/13, 239/135, 136, 337, 352, 11, 589, 601; 169/43, 169/45, 46, 19, 20, 26, 68, 6, 12, 27, 72, 169/76–78

See application file for complete search history.

(56) References Cited

U.S. PATENT DOCUMENTS

| | | | |
|---|---|---|---|
| 3,653,444 A | 4/1972 | Livingston | |
| 3,731,876 A * | 5/1973 | Showalter | 239/13 |
| 3,762,378 A | 10/1973 | Bitonti | |
| 3,868,939 A * | 3/1975 | Friese et al. | 123/179.15 |
| 4,254,833 A * | 3/1981 | Perry | 169/76 |
| 4,522,183 A | 6/1985 | Meier et al. | |
| 5,449,041 A * | 9/1995 | Galbraith | 169/11 |
| 5,645,225 A * | 7/1997 | Hasegawa et al. | 239/533.12 |
| 5,678,637 A | 10/1997 | O'Connell | |
| 5,865,156 A * | 2/1999 | Feucht et al. | 123/446 |
| 6,213,104 B1 | 4/2001 | Ishikiriyama et al. | |
| 6,543,420 B2 * | 4/2003 | Kohketsu et al. | 123/447 |
| 2002/0079377 A1 | 6/2002 | Nichols | |
| 2003/0088207 A1 | 5/2003 | Rogatchev et al. | |
| 2005/0045179 A1 | 3/2005 | Faison, Jr. et al. | |
| 2009/0212125 A1 | 8/2009 | McIntosh et al. | |
| 2010/0031957 A1 | 2/2010 | McIntosh et al. | |

FOREIGN PATENT DOCUMENTS

| | | |
|---|---|---|
| CH | 324334 A | 9/1957 |
| DE | 29602969 U1 | 8/1996 |
| DE | 19637025 A1 | 3/1998 |
| DE | 20310436 U1 | 12/2003 |
| EP | 0820780 A1 | 1/1998 |
| FR | 2047010 A1 | 3/1971 |
| GB | 2202440 A | 9/1988 |

(Continued)

OTHER PUBLICATIONS

International Search Report and Written Opinion of the International Searching Authority, mailed Dec. 18, 2006, for corresponding International Application No. PCT/GB2006/003568.

(Continued)

*Primary Examiner* — Davis Hwu

(74) *Attorney, Agent, or Firm* — Klarquist Sparkman, LLP

(57) ABSTRACT

A method and apparatus is disclosed for ejecting material. The ejected material is ejected as liquid and liquid vapour via an explosive process which can provide a very fast ejection as well as an ejection which has a large throw.

31 Claims, 16 Drawing Sheets

FOREIGN PATENT DOCUMENTS

| | | |
|---|---|---|
| SU | 792645 | 12/1985 |
| WO | WO 95/14450 | 6/1995 |
| WO | WO2007/034229 A1 | 3/2007 |
| WO | WO2007/034230 A1 | 3/2007 |

OTHER PUBLICATIONS

International Search Report and Written Opinion of the International Searching Authority, mailed Dec. 27, 2006, for corresponding International Application No. PCT/GB2006/003576.

International Search Report and Written Opinion of the International Searching Authority, mailed Feb. 13, 2007, for corresponding International Application No. PCT/GB2006/003582.

International Preliminary Examination Report on Patentability of the International Searching Authority, mailed Mar. 26, 2008, for International Application No. PCT/GB2006/003568, 10 pages.

International Preliminary Examination Report on Patentability of the the International Searching Authority, mailed Mar. 26, 2008, for International Application No. PCT/GB2006/003576, 8 pages.

International Preliminary Examination Report on Patentability of the of the International Searching Authority, mailed Mar. 26, 2008, for International Application No. PCT/GB2006/003582, 5 pages.

Office Action from the United States Patent & Trademark Office in U.S. Appl. No. 11/992,565, dated Jan. 5, 2011.

* cited by examiner

VAPOUR EXPLOSION CHAMBER

This application claims the benefit of U.S. Provisional Application No. 60/720,716, filed Sep. 26, 2005, which is incorporated herein by reference.

BACKGROUND

The present invention relates to a method and apparatus for ejecting target mass. In particular, but not exclusively, the present invention provides a method and apparatus for a fast mass ejection device able to eject liquid and liquid vapour quickly and over relatively long distances from an ejection chamber in which a quantity of liquid is stored.

There is a need in a number of industries for mass ejection devices. That is to say, devices which will send out a spray of liquid and liquid vapour at a fixed or variable rate and over a desired distance. Preferably there is a need for a spray of liquid and liquid vapour to occur at a fast rate and over a great distance. In such systems the term "throw" is often referred to as a characteristic of a spray. The throw of material is defined as the distance travelled divided by the length of a chamber from which the spray is ejected.

Various examples of mass ejection devices are known such as fire extinguishers, ink jet printers, air bag igniters, fuel injectors for motor engines and gas turbines, etc. In each of these there are specific problems associated with the device in question, however, for each applied technology there is a continuing desire to be able to eject liquid and liquid vapour quickly and over a large distance.

By way of example of a problem specific to an application of mass ejection systems, reference is made to a gas turbine reigniter. In the igniter of a gas turbine, the conventional approach to reignite gas in a combustion chamber is to pass a current between two electrodes of a reigniter and create for a short while a mixture of electrically charged radicals. This is illustrated more clearly in FIG. 1 in which a conventional reigniter 10 is shown including an outer electrode 11 which is generally cylindrical in shape with an internally located pellet 12. A central electrode 13 is located within the pellet and by passing a current between the two electrodes 11, 13 a mixture of electrically charged radicals (that is when the gas molecules split temporarily into charged components referred to as a plasma). This plasma only lasts for a fraction of a second before recombining and losing its charge. The charge is then used to ignite combustion in a main combustion chamber of the main engine. A problem with such known reigniters is in getting the mixture to be ejected as ejected material via the exit orifice 14 far enough and to remain charged long enough to perform its objective function. The ejected material 15 has been used to ignite the kerosene or other usual gas turbine engine fuel.

SUMMARY

It is an aim of certain embodiments disclosed herein to provide an apparatus and method for ejecting material whereby liquid and liquid vapour are ejected from a chamber, the ejected material having desirable characteristics such as speed of ejection and distance travelled by the ejected material.

It is an aim of certain disclosed embodiments to provide an apparatus and method for providing a fast mass ejector. Desirably, such fast mass ejectors will overcome problems specific to their application such as fuel injectors and gas turbine reigniters etc.

According to a first aspect, there is provided apparatus for ejecting material, comprising:
an ejection chamber arranged to hold a portion of a selected liquid;
an inlet valve arranged to selectively open to thereby transfer liquid into the ejection chamber; and
an exit valve arranged to selectively open to eject material from said ejection chamber as liquid vapour and/or liquid when at least one parameter associated with said ejection chamber satisfies a predetermined condition.

According to a second aspect, there is provided apparatus for ejecting material, comprising:
an ejection chamber arranged to hold a portion of a selected liquid;
an inlet valve arranged to selectively open to thereby transfer liquid into the ejection chamber; and
an exit valve arranged to selectively open to eject material from said ejection chamber as liquid vapour and/or liquid when at least one parameter associated with the ejection chamber satisfies a predetermined condition; wherein
liquid in the ejection chamber is heated above a boiling point, associated with said liquid, prior to the exit valve being opened.

According to a third aspect, there is provided a method for ejecting material, comprising the steps of:
holding a portion of a selected liquid in an ejection chamber;
increasing at least one parameter of the liquid in the ejection chamber;
selectively opening an exit valve of the ejection chamber when the parameter associated with the ejection chamber satisfies a predetermined condition; and
ejecting liquid vapour and/or liquid from the ejection chamber via the exit valve.

According to a fourth aspect, there is provided an apparatus for ejecting material, comprising;
a chamber for holding a body of a selected liquid;
an inlet valve via which the selected liquid can be introduced into the chamber;
an exit valve arranged to open to allow contents from the chamber to be ejected when a predetermined parameter is satisfied; and
means for increasing pressure of the liquid in the chamber; wherein
liquid and liquid vapour are ejected from the chamber via the exit valve.

Desirably said means for increasing pressure comprises a heating element arranged to heat the body of liquid located in the chamber.

Desirably said exit valve is arranged to open when the pressure within the chamber reaches a predetermined value.

Desirably said inlet valve is arranged to open to allow liquid to be introduced into the chamber subsequent to the contents of the chamber previously being ejected via the opening of the exit valve.

Desirably said chamber further comprises a narrow neck region along which liquid and vapour is ejected.

Desirably the liquid and vapour are ejected via a vapour explosion process when the exit valve opens.

Desirably said liquid is water.

Desirably said liquid is a flammable liquid, for example kerosene or petrol.

Desirably said exit valve is set to open at 1.1 bar pressure.

Desirably said means for increasing pressure comprises means for heating the liquid above its boiling point at atmospheric pressure.

Desirably said chamber diameter is in the range of 1 mm to 1 meter.

Desirably said chamber is spherical in shape.

Desirably said chamber is heart-shaped.

Desirably said exit valve is located at an apex region of said heart-shaped chamber.

Desirably said chamber is substantially cylindrical in shape.

According to a fifth aspect, there is provided a method for ejecting material from a chamber, comprising the steps of:

introducing a selected liquid into the chamber via an inlet valve;

increasing pressure of the liquid in the chamber;

opening an exit valve when a predetermined parameter is satisfied; and ejecting liquid and liquid vapour from the chamber via the exit valve.

Desirably the method further comprises the steps of heating liquid located in the chamber via a heating element previous to the step of opening the exit valve.

Desirably the method further comprises the steps of determining when a predetermined parameter is satisfied and opening the exit valve responsive thereto.

Desirably the method further comprises the steps of heating the liquid in the chamber to a temperature above its boiling temperature at the pressure of gas located at a downstream position from the exit valve.

Desirably the liquid and liquid vapour are ejected as a spray having a throw greater than 20.

Desirably said liquid and liquid vapour are ejected as a spray having a throw greater than 100.

In particular embodiments, an ejection chamber is provided in which liquid and liquid vapour are exploded from an exit orifice. The vapour explosion has the effect that target material is blasted out from the ejection chamber very rapidly and over distances not previously obtainable with known techniques.

Using a vapour explosion gives a longer throw than classical fuel injectors. For example, the throw of a liquid and liquid vapour explosion in accordance with certain embodiments may be around 200 to 300 times or more its corresponding chamber length. For a classical fuel injector similar values would be of the order of 10 to 20 times an injection chamber size. This is because of the dynamics of the vapour explosion which occurs as a large pressure of liquid in an ejection chamber is cyclically built up and then released.

Certain disclosed embodiments can provide a fuel ignition system in which the vapour explosion chamber used to eject material can be used to inject fuel (used as its liquid) into a combustion chamber. The injected fuel is mostly vaporized (around 70% or more of ejected mass is fuel vapour) before exiting the injector nozzle. This is of a significant benefit because any liquid fuel has first to be vaporized to be able to react with air (oxygen). With known fuel injectors, liquid fuel must first be atomised to enhance its vaporization. This step in exemplary embodiments is not required since the injector injects readily vaporized or already vaporized fuel. This significantly facilitates the ignition and combustion processes.

Certain embodiments used as fuel injectors also provide the advantage that the new injector requires much lower pressures to inject an amount of fuel relative to known injectors injecting that same amount of fuel. For example, in prior art petrol engines which operate at much lower pressures than diesel ones, the injection pressure is about 100 bars. Certain embodiments provide a fuel injector which requires pressures of only 10 to 15 bars. This makes the system cheaper to make and to maintain.

Certain embodiments provide a fuel injector having a longer throw than known prior art fuel injectors. This has the advantage of having a more rapid and better mixing and vaporization of the fuel.

Certain embodiments provide a gas turbine reigniter which is able to reignite fuel in a combustion chamber of a gas turbine more quickly and in a more controlled manner than is possible with previously known techniques.

Certain embodiments provide a pilot flame igniter able to ignite target fuel very quickly and over a great distance relative to the size of the igniter apparatus and amount of fuel used. By repeatedly ejecting fuel from the ejection chamber the pilot igniter can be kept alight.

Certain embodiments provide a propulsion unit which can be used for vehicles. The propulsion unit can be small scale and even nano scale and much lighter than known propulsion units since the ejection used to propel a vehicle is very powerful, fast and occurs energetically over a great distance.

Certain embodiments provide a fire extinguisher system which can either be portable or fixed, for use internally in buildings or vehicles, which, once triggered, can operate very rapidly to eject fire suppressant material at the heart of a fire. The use of spray has been found to be beneficial when fighting fires.

BRIEF DESCRIPTION OF THE DRAWINGS

Embodiments of the present invention will now be described hereinafter, by way of example only, with reference to the accompanying drawings in which.

DETAILED DESCRIPTION

Figure 1:
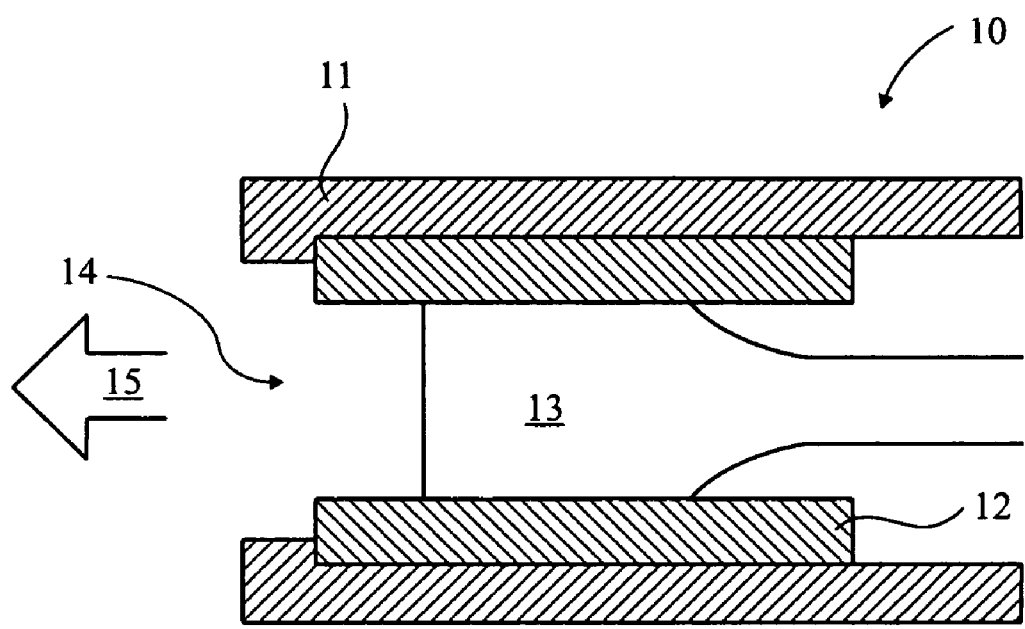
FIG. 1 illustrates a prior art gas turbine reigniter.

In the drawings like reference numerals refer to like parts.

Figure 2:
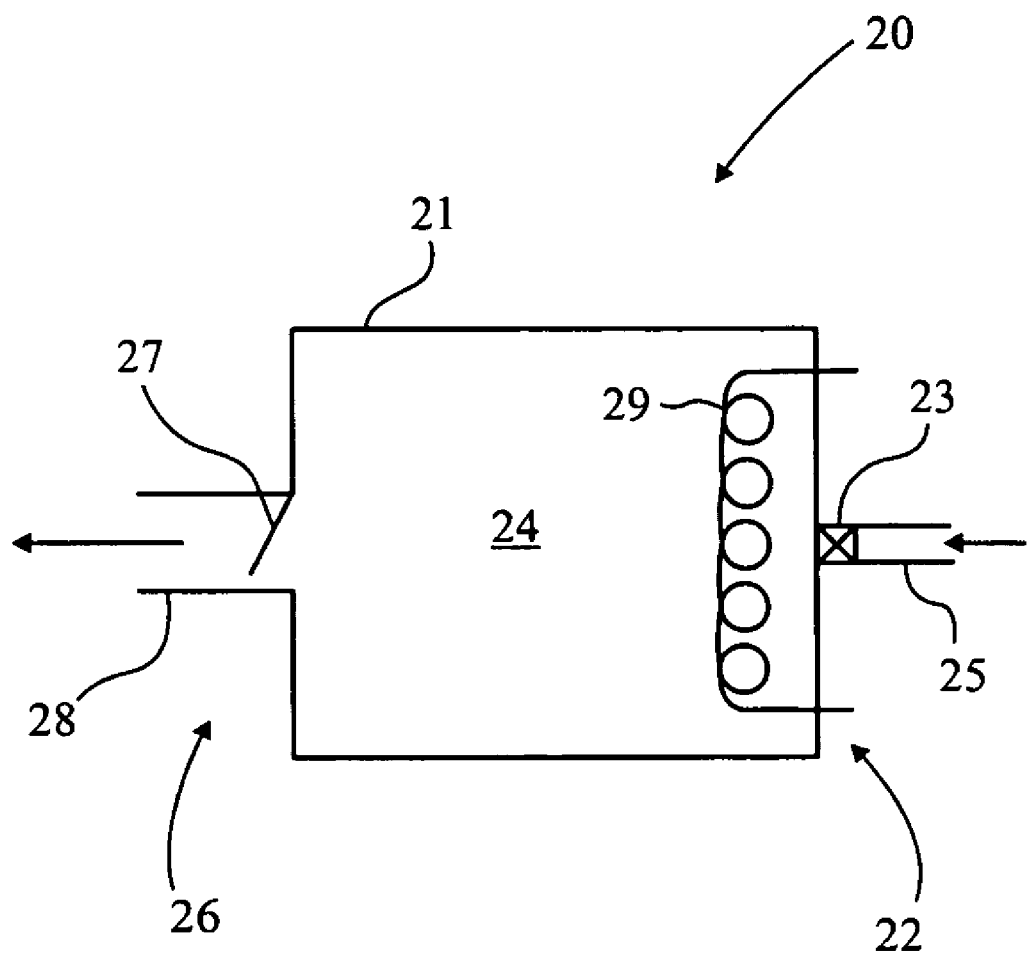
FIG. 2 illustrates apparatus for ejecting material.

FIG. 2 illustrates an ejection system 20 for ejecting liquid and liquid vapour via a vapour explosion process in accordance with one embodiment. An ejection chamber 21 is formed in a generally cylindrical shape from a material such as steel or other rigid material which is able to withstand substantial pressure and temperature changes. It will be understood that embodiments of the present invention are not limited to combustion chambers having this specific shape, nor indeed to combustion chambers formed from steel. At a first end region of the chamber 21, signified by reference numeral 22, an inlet valve 23 is located so as to allow a selected liquid such as water to enter the central region 24 of the chamber via an associated inlet pipe 25. At a further end region 26 of the chamber 21 is located an exit valve 27 which opens to allow material to be ejected from the chamber region 24 through a nozzle region 28.

A heating element 29 is provided by an electric heater located in the ejection chamber. The electric heater is connected to a power source (not shown) so that when turned on the heater operates to heat up a body of liquid located in the region 24 of the chamber. It will be understood that according to further embodiments (some of which are described hereinbelow) other ways of raising the pressure and temperature of liquid in the ejection chamber may be provided.

As shown in FIG. 2, the pressure of a liquid in the central region 24 of the chamber may be increased by heating the liquid in it. Prior to this stage the exit valve 27 is closed to prevent outgress of liquid. The inlet valve 23 is opened to allow liquid water to enter the chamber until the chamber is full or contains a predetermined quantity of liquid. The inlet valve is then closed sealing the body of liquid thereby located in the chamber. The heater element then operates to heat the liquid. As a result of this the liquid expands due to thermal expansion raising the pressure of the liquid inside the chamber. Whilst the heating can be done by heating elements, it would of course be possible to have a preheated liquid supply at the inlet to the chamber under high pressure. If this technique is adopted the pressure rise in the chamber is performed by a pump (not shown) which is feeding the liquid supply into the chamber through the inlet valve. By heating the water the pressure in the chamber therefore rises. Also, the temperature rises. The exit valve is controlled so that the valve "blows" so as to open at a predefined/predetermined pressure. The pressure can be monitored by one or more pressure sensors such as pressure transducers located in the chamber or close to the chamber. The water or other liquid in the chamber is thus heated by an electrical element (much like an electric kettle) and then rises to a boiling temperature well above its boiling temperature at atmospheric pressure. The temperature rises above the boiling temperature at atmospheric pressure because the water is kept in the chamber by both an inlet valve which closes prior to the water being heated and an exit valve which only allows a release once the system has reached a particular pressure. At this pressure the valve blows in a similar way to a pressure cooker. A vapour explosion then takes place which causes a combination of liquid and liquid vapour (if the liquid is water the liquid vapour would be steam) to exit from the chamber. When the exit valve opens the steam and water mixture is ejected via the opening 28.

When the exit valve opens initially a first phase to be ejected is a liquid phase in the form of shattered liquid in a spray. This ejection occurs in a matter of microseconds subsequent to the exit valve opening. This extremely rapid ejection of liquid has particular advantages. A few microseconds later a mixture of liquid and liquid vapour is ejected. Some microseconds later a mixture containing slightly less liquid and more vapour is ejected.

As material is ejected from the ejection chamber, the pressure drops. When the pressure has dropped back to an ambient or second predetermined pressure, the exit valve is closed and the inlet valve opened again to introduce new liquid material into the chamber. This restarts the cycle. Consequently a repeated cycle of steam/water mixture or other liquid/liquid vapour is exhausted from the outlet once sufficient pressure is generated by heating up the new supply of liquid water.

The size of the chamber can vary and may, for example, be less than a centimeter in diameter. For example, the chamber may even be at the nano size to mm diameter. Alternatively, the chamber may be a meter or more in diameter. It will be appreciated that as the size of the chamber increases, the frequency of the blasts will reduce since the time taken to increase the pressure will increase appropriately. It will be understood that as the size of the chamber is increased according to specific uses, larger pumps and/or valves will be required.

Figure 3:
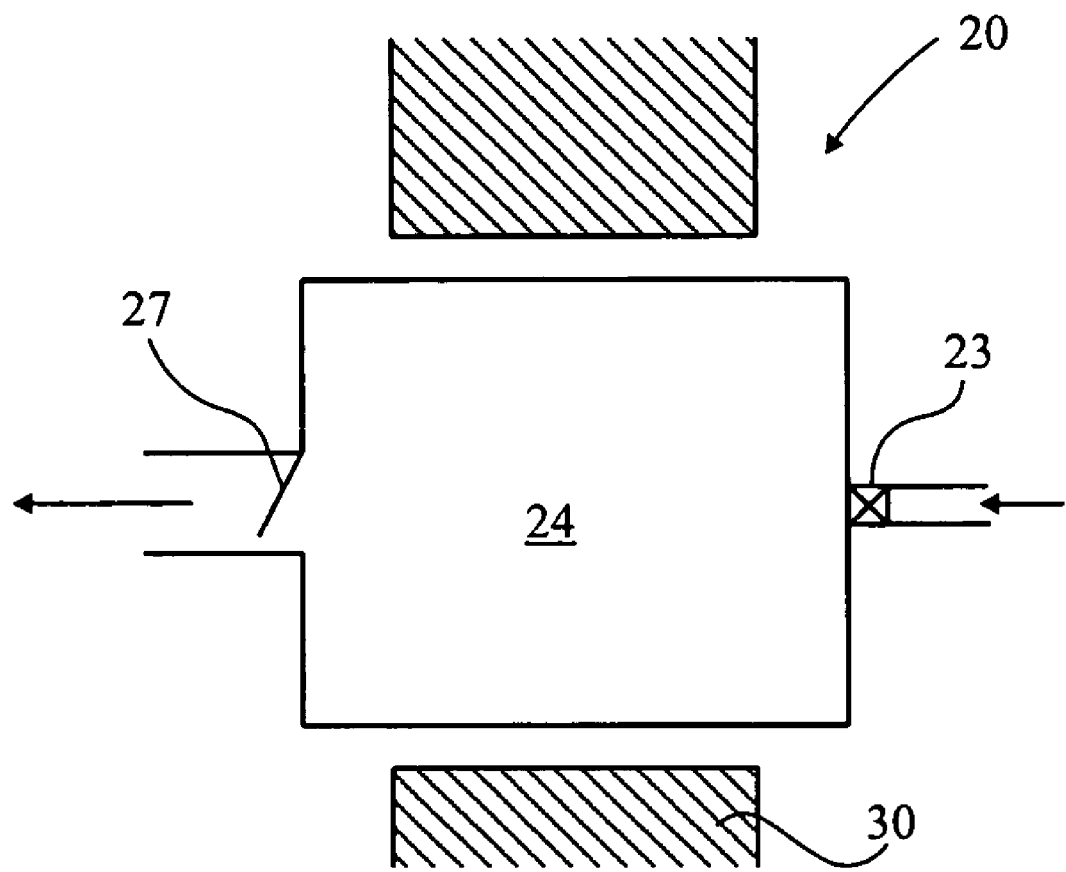
FIG. 3 illustrates an alternative embodiment of apparatus for ejecting material.

FIG. 3 illustrates an alternative embodiment of the ejection apparatus which shares many features in common with the embodiments shown in FIG. 2. The embodiment illustrated in FIG. 3 uses a heat exchanger 30 which encloses a side wall portion of the chamber to heat liquid in the chamber. This manner of heating liquid is particularly advantageous when the liquid ejected is not water but is a fuel which is subsequently burned. The generation of this heat at a location downstream of the exit valve can be used to heat the heat exchangers and thus heat the liquid in the chamber.

Figures 4A, 4B:
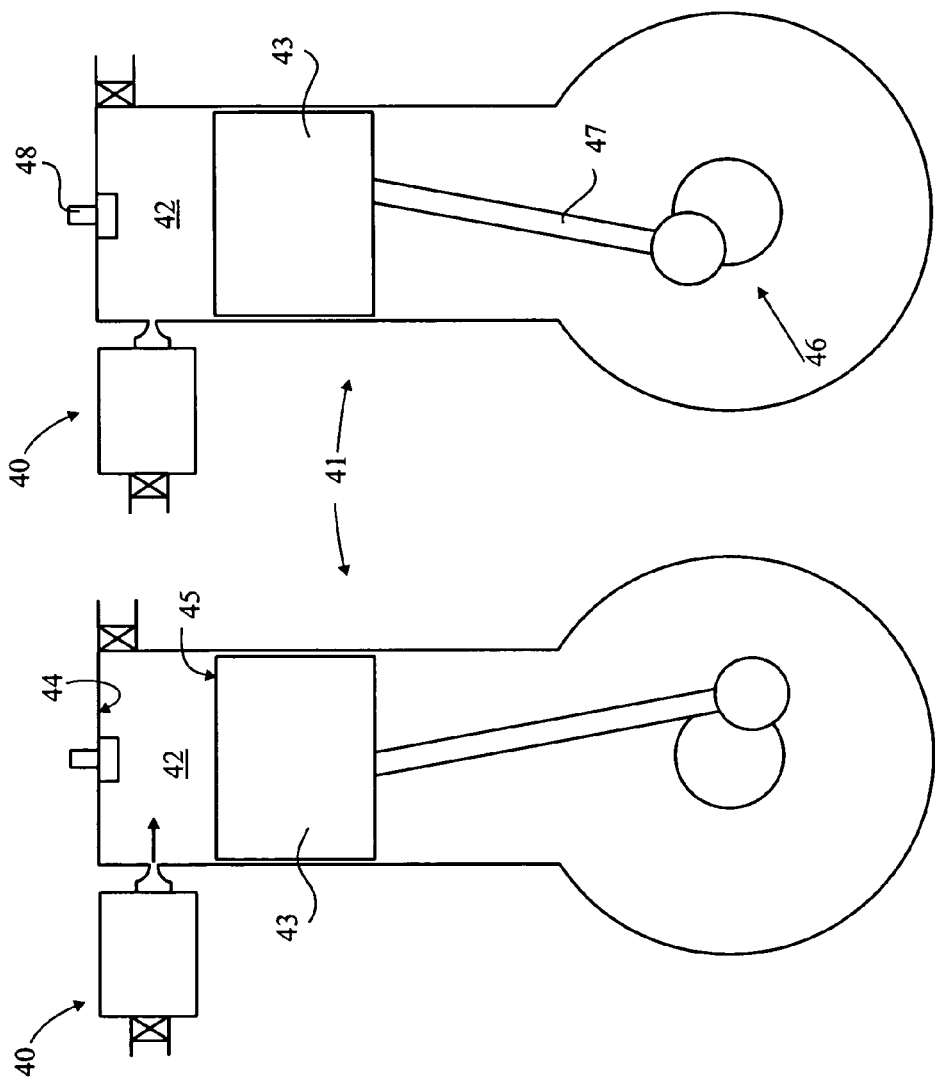
FIG. 4 illustrates a combustion engine.

FIG. 4 illustrates the use of a further embodiment as a fuel injector unit 40. A combustion engine 41 is illustrated in an intake stage (shown in FIG. 4A) and an exhaust phase (illustrated in FIG. 4B). The combustion engine includes a cylindrical combustion chamber 42 closed at a first end by a tight-fitting piston 43 which is arranged to slide within the chamber. The movement of the piston varies the volume in the chamber 42 between the closed end of the chamber 44 and a combustion surface 45 of the piston. An opposed side of the piston connects to a crank shaft 46 via a piston rod 47. The crank shaft transforms the reciprocating motion of the piston into rotary motion.

The combustion engine illustrated in FIG. 4 is a four stroke internal combustion engine, however, it will be understood that embodiments of the present invention are not restricted to use of fuel injectors with such types of engine. Rather a four stroke internal combustion engine is referred to here by way of example only. On the first downward stroke of the piston, fuel is injected via the fuel ejector 40 into the combustion chamber 42.

Prior art fuel injectors use electro-mechanical nozzles and a pre-pressurised fuel to produce a finely atomised spray. Fuel is pressurised within a chamber and an electro-magnetic coil lifts a needle of its seal so fuel can squeeze through the nozzle's aperture through an intake valve. Control of the timings of the release of this pressurised liquid is controlled by electronics. This has the disadvantage of costly and complex materials which are prone to error and require many working parts. Certain embodiments overcome this by replacing the known fuel injector systems with an ejection chamber 40 which ejects liquid fuel and liquid fuel vapour into the combustion chamber 42 via a vapour explosion process as noted above. The vaporized fuel and liquid fuel is ignited via an ignition element such as a spark plug 48.

Figure 5:
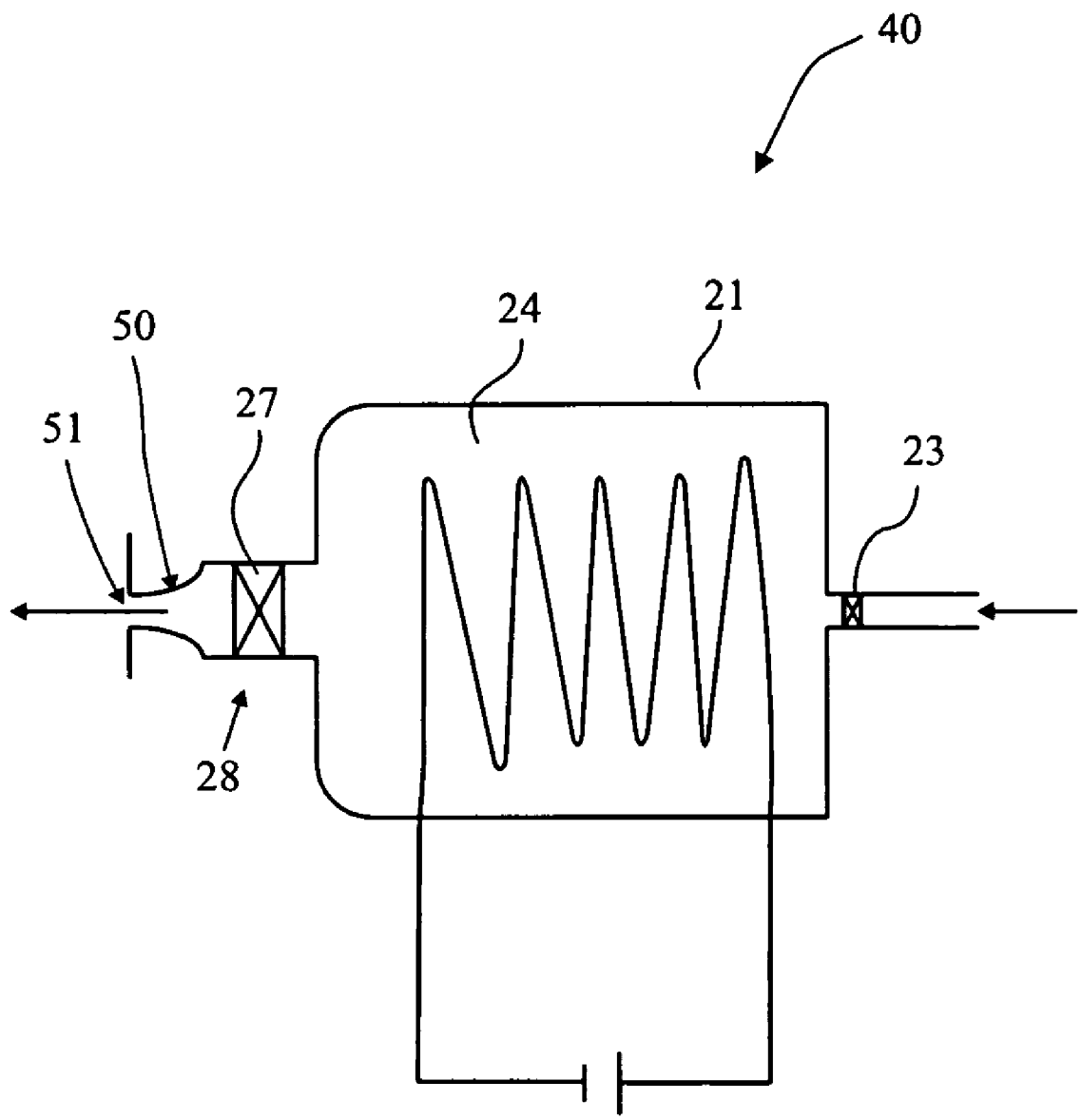
FIG. 5 illustrates a fuel injector.

A fuel injector system in accordance with an exemplary embodiment is shown in more detail in FIG. 5. The fuel injector 40 comprises an ejection chamber 21 defining a space 24 within which liquid fuel can be input via an inlet valve 23. A heating element 29 is used to heat a body of liquid located inside the ejection chamber subsequent to its introduction through the inlet valve. An exit valve 27 constrains the liquid within the chamber until a predetermined pressure is reached. This pressure is greater than atmospheric pressure or the pressure experienced by ejected material downstream (that is to say to the left-hand side shown in FIG. 5). In this way liquid in the chamber can be heated above the boiling point temperature which will be experienced when the exit valve is opened. When the exit valve is thus opened the pressure will drop thus causing the liquid in the ejection chamber to boil rapidly and in an explosive manner due to its elevated temperature above its natural boiling point. It will be noted that for certain fluids, for example, for kerosene and gasoline, the fluids are themselves multi-component fuels which include different hydrocarbons. Each of these has a different boiling point. For gasoline, for example, the boiling points range from 117° C. (for the most volatile component) to 200° C. for the heaviest component and for kerosene the boiling points range from 150° C. to 300° C. In order to have optimum performance it is preferable that the temperature should be kept above the higher boiling point to make sure that all components are going to vaporize. This is, of course, not necessary. For example, where one knows which component has the dominant concentration, then that component's boiling point may be used to fix the temperature ensuring that the rest of the fuel will boil. It will be appreciated that the temperatures given here are examples of the corresponding boiling points at atmospheric pressure. These will be very different at elevated pressures and reference may be made to known databases of thermophysical properties of materials to obtain working pressures. A nozzle 50 provides a narrowing of a neck region 28 and ejected liquid and liquid vapour are ejected through an opening 51 into the combustion chamber 42 of the combustion engine.

An advantage of applying the above-described vapour explosion technology to fuel injection systems is to greatly enhance the throw of the devices and consequently the response of the engines to an increased power output. For an average sized family car, according to known prior art techniques, a normal operating range is 2,000-6,000 rpm with a Formula I car attaining perhaps 17,000 rpm. In accordance with certain embodiments disclosed herein, a time taken for one cycle of a fuel injector which comprises a short ejection phase, followed by a longer refilling and repressurising phase, can be around 5 milliseconds or less. The rate of fuel injection is thus around 12,000 injections per minute. In a common four stroke engine there are typically two revolutions per injection and therefore 24,000 rpm could, in theory, be achieved. In order to avoid disintegration of the engine, some form of limiting constraint may therefore be utilised to slow down the ejection process.

Figure 6:
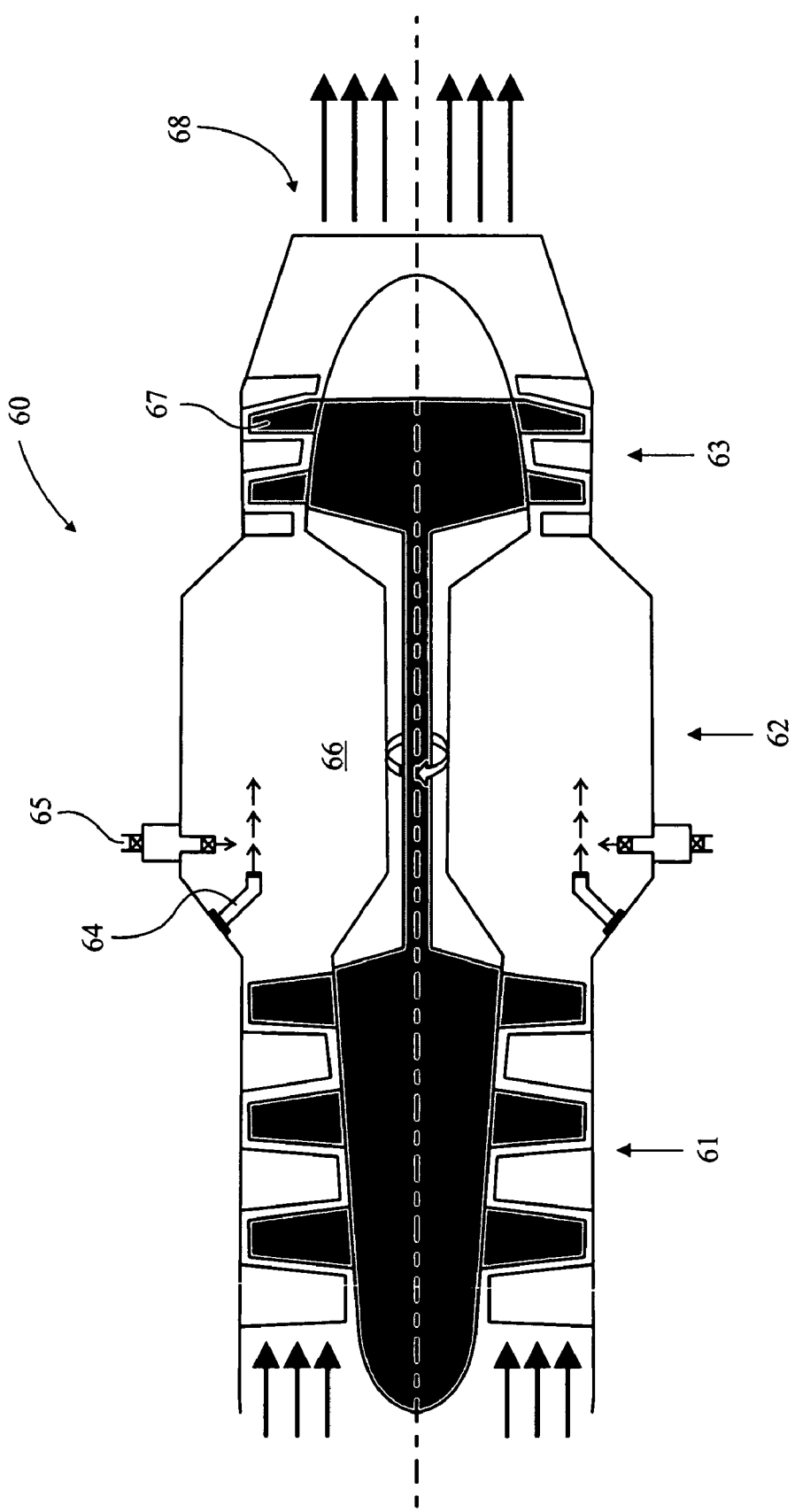
FIG. 6 illustrates a gas turbine.

FIG. 6 illustrates how an embodiment may be applied to provide a gas turbine reigniter. FIG. 6 illustrates a gas turbine 60 comprising three main sections. These are the compressor 61, combustor 62 and turbine 63. Outside air is drawn into the engine by the action of the compressor. The air is mechanically compressed by the motion of the compressor blades consequently the pressure and temperature of the air increases with the corresponding decrease in volume. The mechanical energy used to compress the air is thus converted into kinetic energy in the form of compressed air. The compressed air is then forced through into the combustion section into which fuel is injected via a fuel injector 64. The fuel injector may be of a conventional type or may be of a type previously described hereinabove. A fuel reigniter 65, in accordance with an exemplary embodiment, is then used to ignite the fuel converting the chemical energy into thermal energy in the form of hot expanding gas. Fuel is repeatedly injected into the combustion section to ensure continuous combustion. Rather than repeated injection, fuel may be constantly injected. Volume of gas and temperature increase while the pressure remains substantially constant through the combustor chamber 66. The hot expanding gas's thermal energy is converted to mechanical energy as the turbine 63 is rotated by virtue of the gas acting on fins 67 of the turbines. Hot exhaust gas then exits out via a front end 68 of the gas turbine. The output turbine is connected to the compressor blade thus helping to power the compression of air.

As noted above, known reignition devices (for example as shown in FIG. 1) include complex plasma arrangements to reignite material in the combustion chambers 66 of gas turbines. It will be appreciated that the combustion chamber may contain many fuel injectors distributed throughout the chamber in an advantageous manner and one or more fuel reigniters may be provided to reignite fuel injected by each of the injectors. Alternatively, it will be understood that the locations of the fuel injectors may be carefully designed so that less than one reigniter is required per injector. Gas turbines have many applications such as jet engines in the aerospace/nautical industries, engines for land vehicles, as well as electrical power generation using land based gas turbines.

Figure 7:
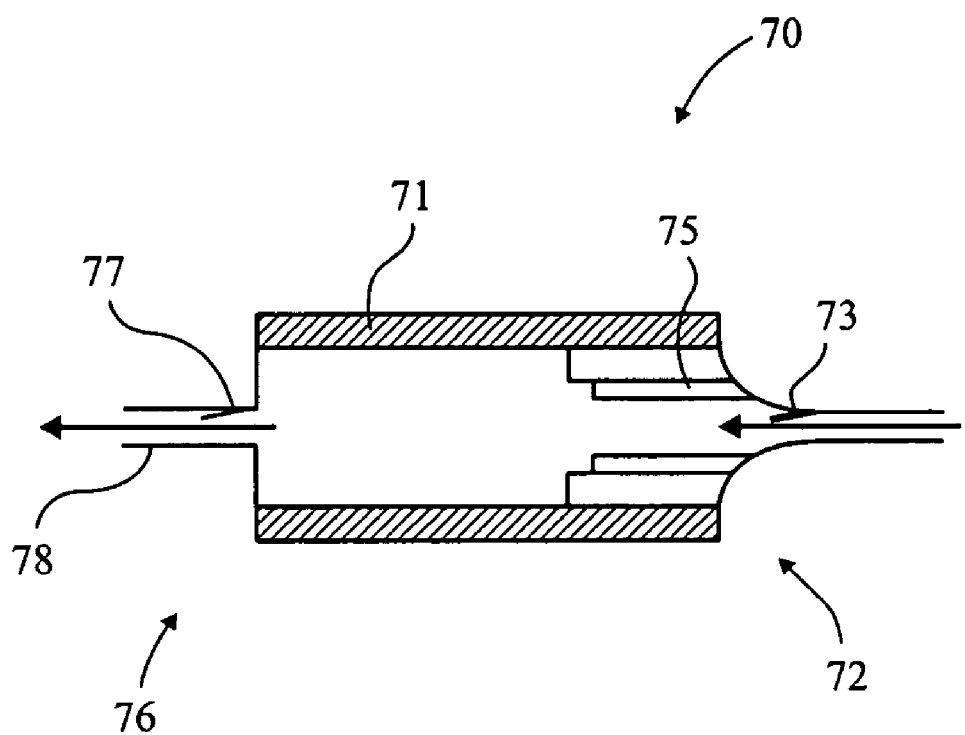
FIG. 7 illustrates a gas turbine reigniter.

FIG. 7 illustrates a gas turbine reigniter 70 in more detail. An outer electrode 71 which is substantially cylindrical in shape forms a side wall for an ejection chamber. At a first end region 72 an inlet of liquid fuel enters via an inlet valve 73. Input fuel enters a central chamber region 74. The input fuel flows through a hole in an inner electrode 75. At a further end 76 of the ejection chamber, an exit valve 77 is located which prevents outgress of the input liquid fuel. When the exit valve 77 is opened liquid and liquid vapour are ejected via a nozzle 78. A central semi-conductor pellet separates the outer and inner electrodes. This element 79 is used to create charged particles to heat the liquid fuel in the chamber. As one or more pressure sensors detect the pressure in the chamber reaching a predetermined value, a current is passed through.

Figure 8:
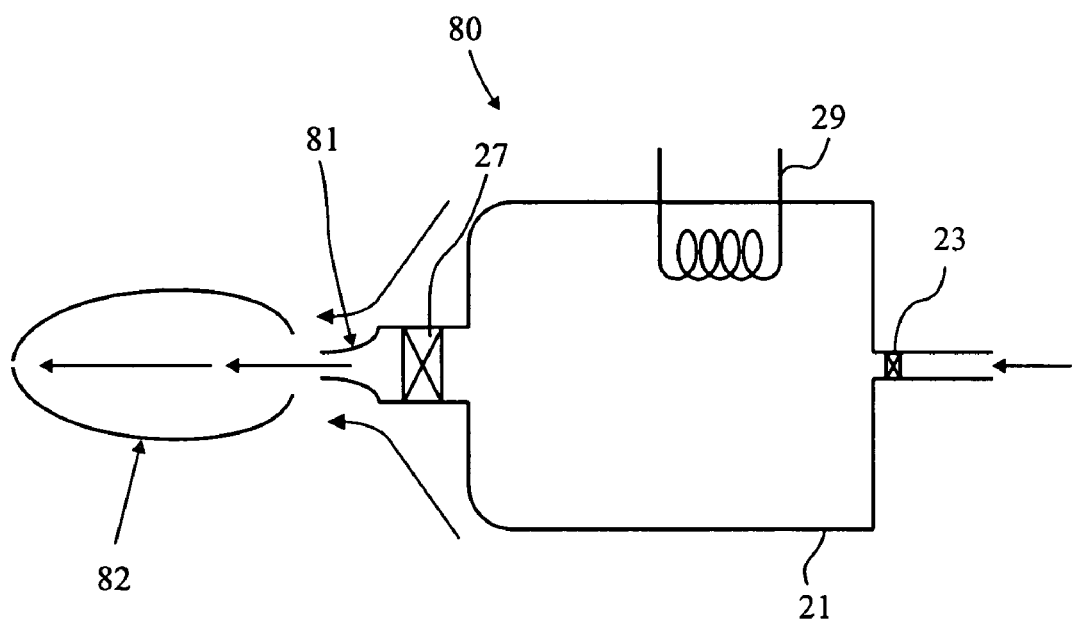
FIG. 8 illustrates a pilot igniter.

FIG. 8 illustrates an application of the vapour explosion technology in accordance with a further embodiment in which a pilot flame igniter is provided. In this sense FIG. 8 illustrates a pilot flame ignition ejection system 80. Flame ignition systems are required for many applications such as in boilers or furnaces or domestic appliances, or domestic gas applications. Prior art ignition systems generally consist of an electronic circuit that produces a spark which consequently lights the fuel. The pilot flame igniter 80 includes a fuel chamber for storing a body of liquid introduced through an inlet valve 23. A heating element such as electric heater 29 heats the fluid as above-described which is allowed to exit the exit valve 27 when a predetermined threshold pressure is reached within the chamber. Liquid fuel and liquid fuel vapour is ejected through a nozzle 81 repeatedly as repeated vapour explosion processes take place rapidly. By virtue of the vapour explosion the fuel vapour and liquid fuel is discharged with a large throw, that is to say, over a large distance away from the nozzle 81. This may be ignited initially by an ignition element (not shown) so that a flame 82 is constantly provided to light further ignitable material. It will be appreciated that the ejection system 80 for the pilot flame provides a repeating ejection process. During an initial stage immediately after opening of the exit valve, ejected material is substantially in the form of a shattered liquid. Subsequent to this, by some tens of microseconds, the ejected material is a mix of liquid and liquid vapour. Still later the ejected material is predominantly vapour. When the exit valve closes so as to allow recharging of the ejection chamber the flame will be unanchored. The dead time caused by the closing of the exit valve is selected so as to be long enough to enable refuelling of the ejection chamber but not so long that the flame burns all fuel and dies. The result will be a pilot igniter having a flame which may perceptively dance up and down but which will not be extinguished.

Figure 9:
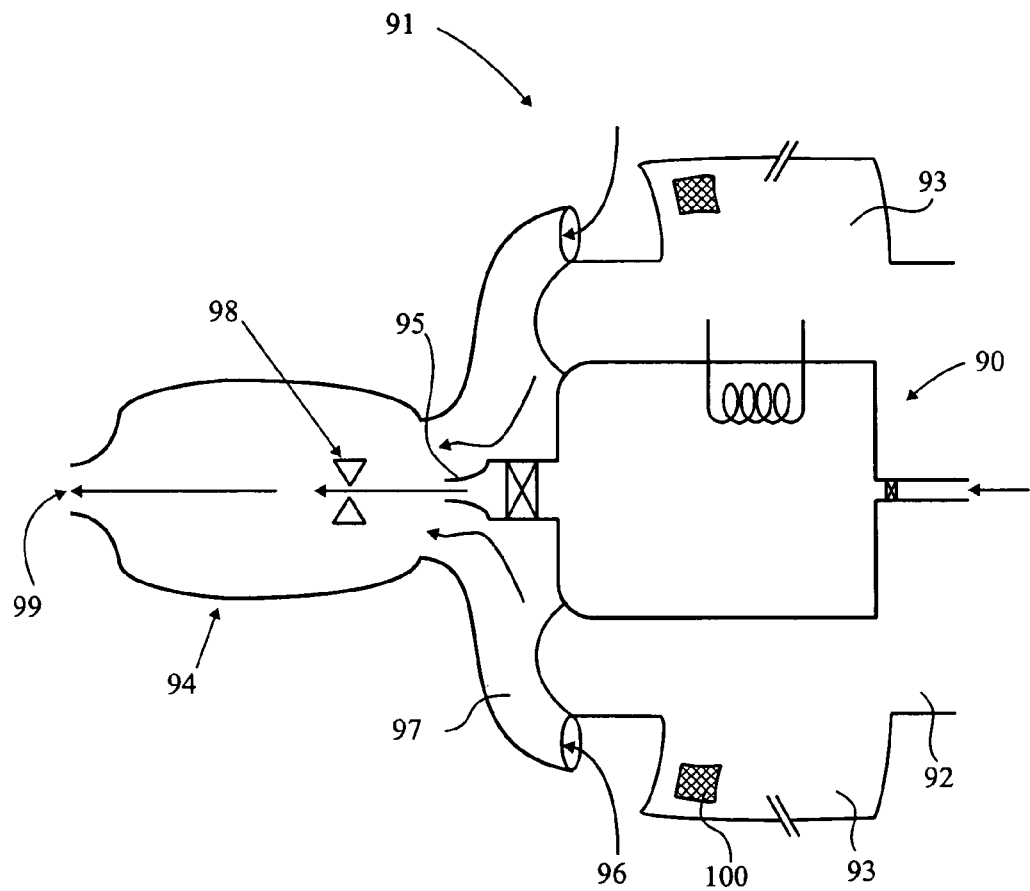
FIG. 9 illustrates a propulsion system for a vehicle.

FIG. 9 illustrates a further embodiment in which an ejection chamber 90 is used to propel a vehicle 91. The vehicle 91 is shown as an unmanned aerial vehicle (UAV). Such vehicles are remotely piloted or self-piloted aircrafts that can carry cameras, sensors, communications equipment or other loads. It will be appreciated that exemplary embodiments can be used to propel other types of vehicle. The UAV includes a vehicle body 92 which includes two wing sections 93 which provide lift for the vehicle. Propulsion is provided by burning liquid fuel and fuel vapour ejected from the ejection chamber system 90 in a combustion chamber 94. There are many types of UAV. Some are the size of a small plane and fly at high altitudes capable of recording and relaying large amounts of information back to a base station. Some vehicles are light enough to be carried by a single human and launched by hand. Micro air vehicles are those vehicles defined as having no dimension larger than 15 cms (6 inches). Certain embodiments are also applicable to micro air vehicles or smaller.

The mass ejection chamber 90 ejects liquid fuel and liquid fuel vapour from a nozzle 95 as described hereinabove. Air is drawn into an air intake 96 and passes down inlet passages 97 where the air mixes with the fuel which is ignited by an ignition element 98, such as a spark igniter. The combustion chamber 94 constrains the combustion process and includes at least one exit orifice 99 through which burnt combustion gases and flame can escape. Propulsion is achieved by the expanding hot exhaust gases. The vapour explosion chamber 90 is of a small size so that the overall dimension of the device may be of the order of 5-10 cms in length.

Solar panels 100 are provided to provide an energy source for the heating element and control of the igniter element 98 if required. Alternatively, an onboard light weight battery may provide the power source. As a further alternative, continuous heat exchange from the exhaust gases can provide the energy to heat inlet fuel.

Figure 10A:
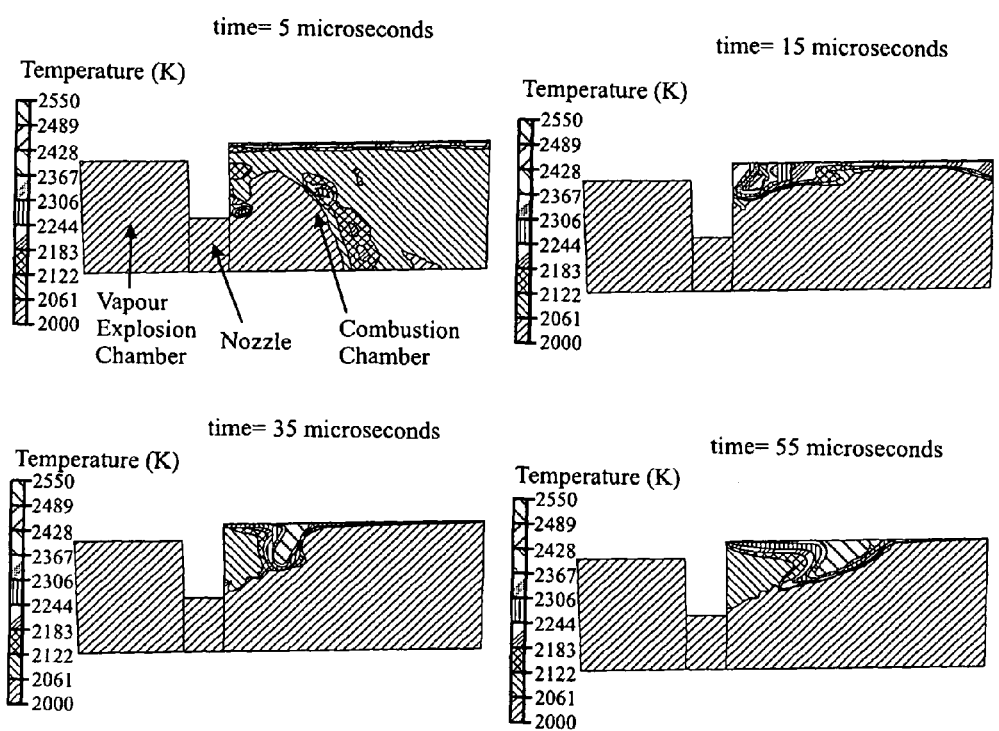
FIG. 10 illustrates combustion in a combustion chamber.
Figure 10B:
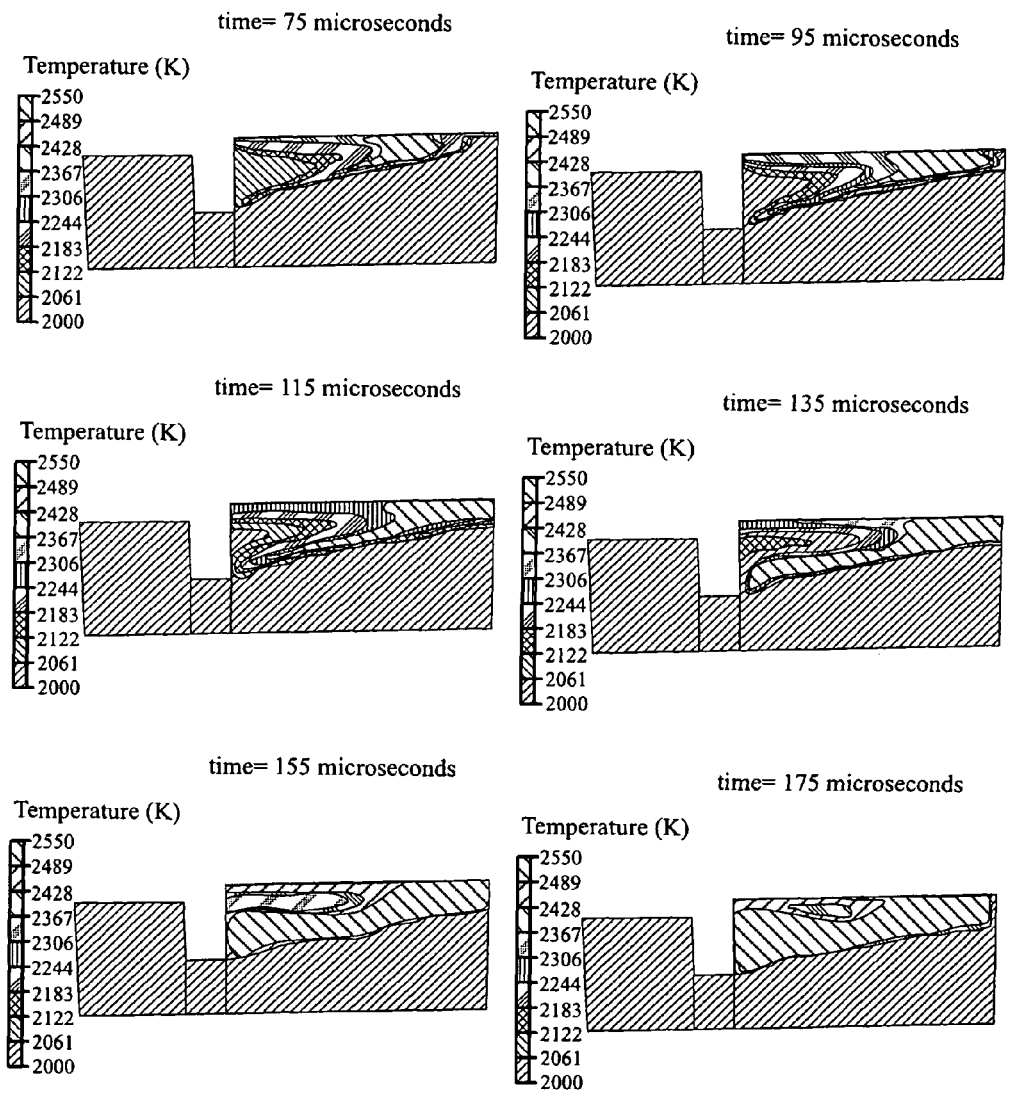
Figure 11:
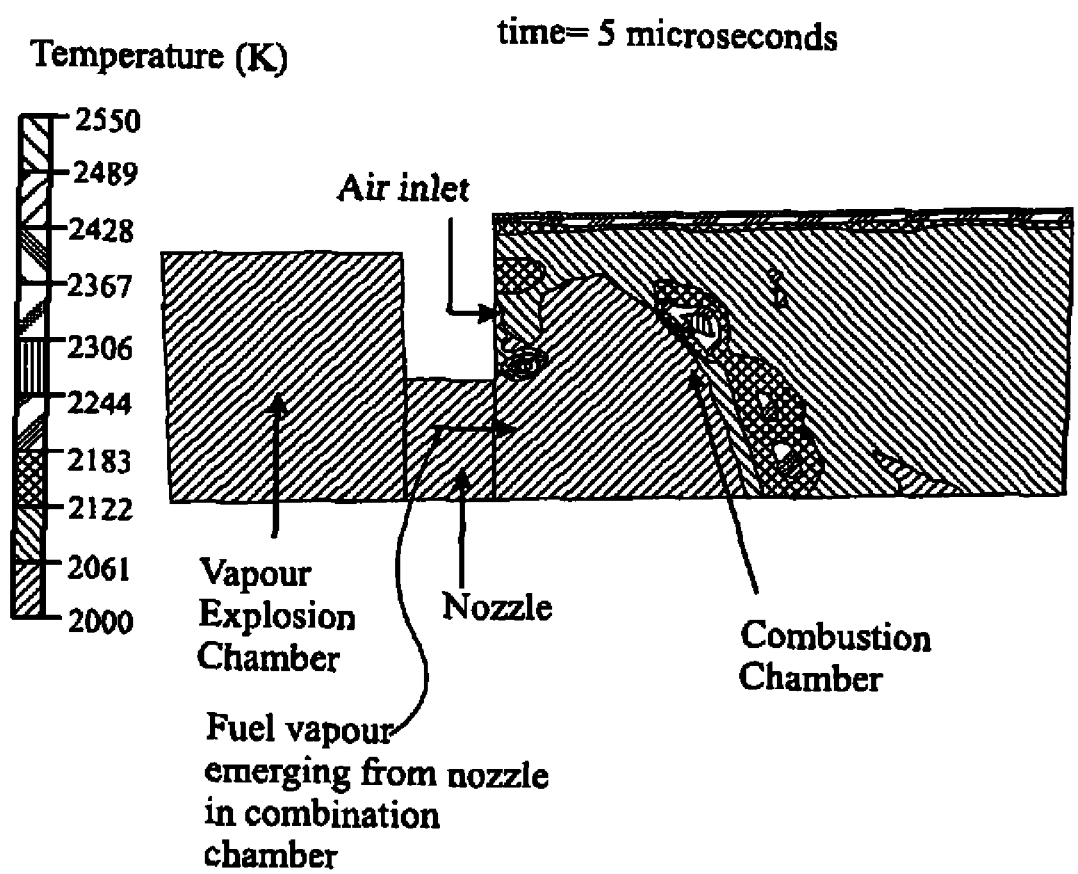
FIG. 11 illustrates an air inlet.

FIG. 10 illustrates a cycle in the vapour explosion chamber as shown in FIG. 9. In this example the vapour explosion chamber 90 and combustion chamber are 330 microns and 370 microns in diameter and 300 microns and 700 microns in length respectively. A hydrocarbon liquid fuel is vaporized in the vapour explosion chamber and the vapour is ejected from the chamber through a nozzle to the combustion chamber where it mixes with air. The air is introduced through a further inlet as shown more clearly in FIG. 11. Via an ignition device, which may be heat or flame from a preceding cycle (as shown) or a separate igniter element such as a spark igniter, the combustion is triggered and within some microseconds a flame is filling the combustion chamber. In these figures the colour/shade contours of temperature are given at different times showing the development of a flame and corresponding temperature changes over time. Since the pressure relief exit valve has to be closed for some milliseconds between each cycle for fuel replenishment in order to keep a stable flame in the combustion chamber, it is preferable to use more than one and most preferably between 3 and 10 vapour explosion devices to eject fuel into the combustion chamber. The vapour explosion devices are positioned in a way that they inject at an identical or close to identical point in space and in the same direction but having equal or otherwise selected time delays with respect to each other in the beginning of their injection times.

Figure 12:
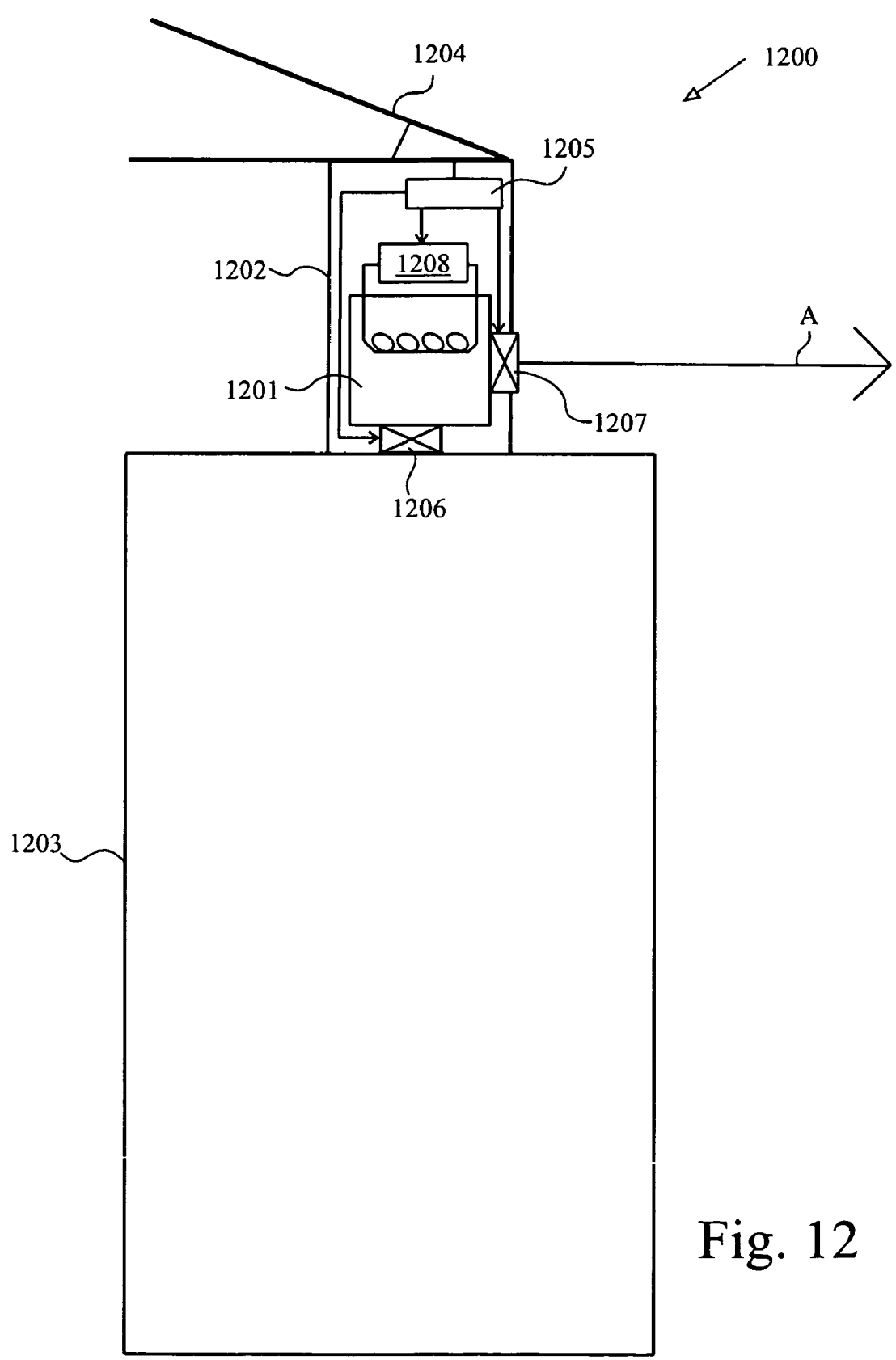
FIG. 12 illustrates a hand held fire extinguisher.

FIG. 12 illustrates an ejection system 1200 for ejecting fire suppressing liquid and fire suppressing liquid vapour via a vapour explosion process in accordance with a further embodiment. An ejection chamber 1201 is formed in a neck region 1202 of the fire extinguisher 1200. A fluid reservoir 1203 contains a large quantity of liquid fuel suppressant such as water. A handle 1204 is used to activate the fire extinguisher by a user when the existence of a fire is determined. Activation of the handle initiates a control unit 1205 to produce drive units for controlling opening and closing of an inlet valve 1206 and outlet valve 1207. Liquid and liquid vapour are ejected from the chamber 1201 in the direction shown by arrow A in FIG. 12. Drive signals from the control box 1205 are also used to control a power source 1208 which controls an electric heater in the chamber 1201. The heater can be used to increase the pressure of liquid in the ejection chamber 1201 as described hereinabove. The liquid reservoir 1203 is also pressurised so that liquid is rapidly replenished in the chamber. The pressure can be so great as to increase the pressure of the liquid in the ejection chamber above atmospheric pressure.

Figure 13:
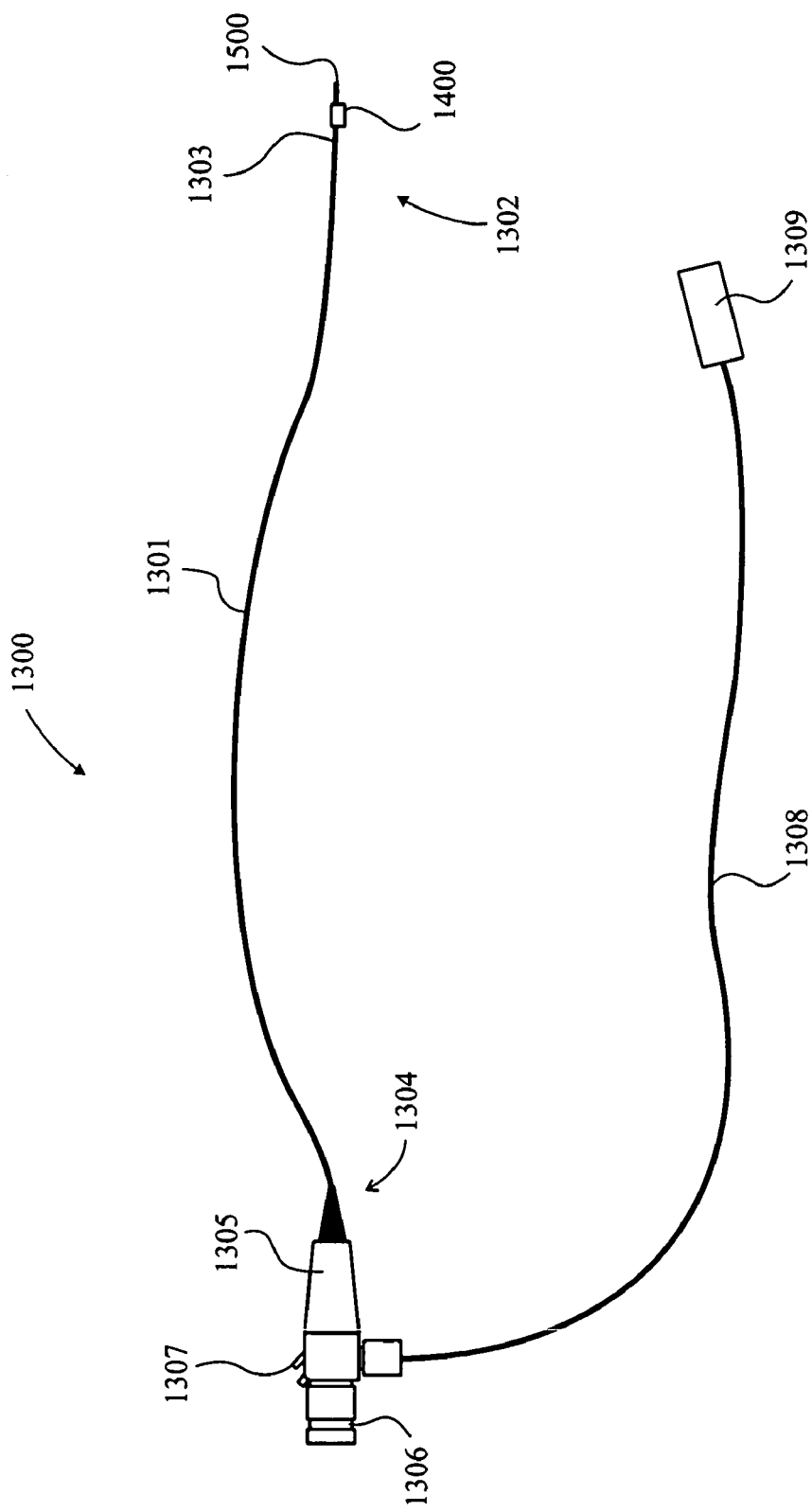
FIG. 13 illustrates delivery of medicaments.

FIG. 13 illustrates how the vapour explosion technology can be applied in accordance with a further embodiment to provide a medical drug delivery apparatus and method or apparatus and method for clearing a blockage in a patient. FIG. 13 illustrates an endoscope 1300 which has a flexible and manoeuvrable shaft 1301 which may be located in an intestinal track or respiratory system or cardiovascular system portion of a human body. A distal end region 1302 of the flexible shaft 1301 includes a flexible tip 1303. The tip allows an end stop device 1400 (shown more clearly in FIG. 14) to be manoeuvred with respect to a patient's body and allows the end of the shaft to be positioned by a surgeon. A proximal end 1304 of the shaft 1301 terminates in an endoscope body portion 1305 which includes an eye piece 1306 and openings 1307 for auxiliary equipment. A further cable 1308 connects the endoscope body 1305 to an input connection 1309 which supplies any required light, air, water or other needed utility to the endoscope.

Figure 14:
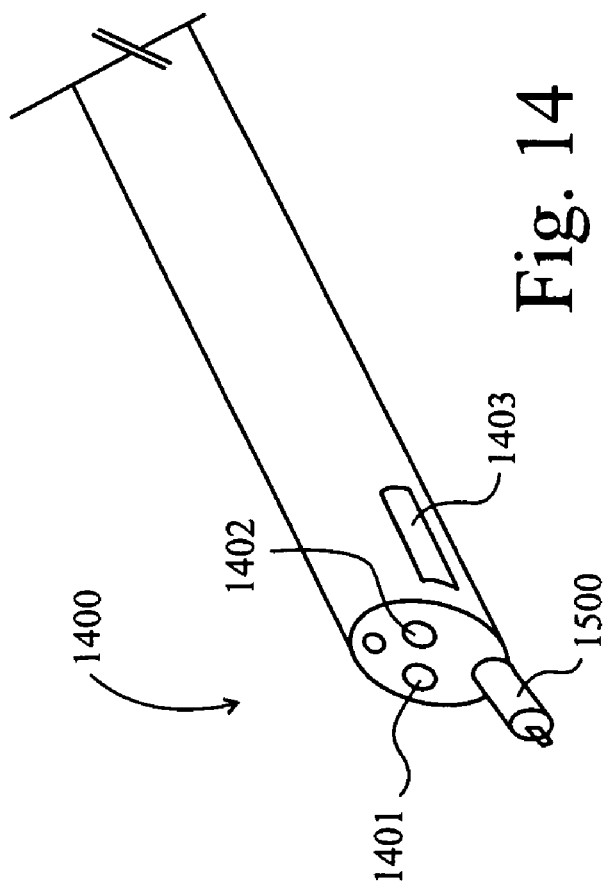
FIG. 14 illustrates an end of an endoscope.

As shown more clearly in FIG. 14, the end of the endoscope 1400 includes a light 1401 for illuminating a region surrounding the end of the endoscope for a surgeon and a camera 1402 for providing visual images of the region of the patient. The signals from the camera 1402 may be provided to the eye piece 1306 or outputting signals via the connection 1309 or via an opening 1307 so that images are displayed on a display, such as an LCD screen.

Figure 15:
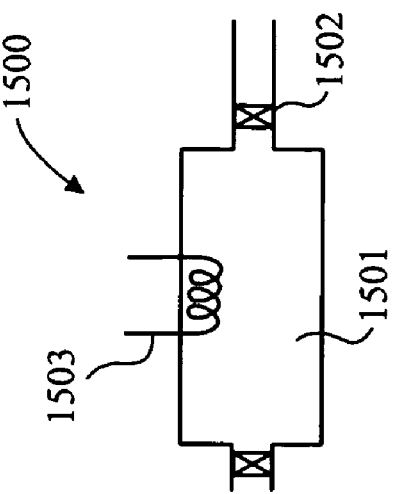
FIG. 15 illustrates how a medicament can be delivered.

The end 1400 of the endoscope 1300 also includes a medicament delivery chamber 1500 as seen more clearly in FIG. 15. Power and control signals are supplied to the medicament delivery chamber 1500 via controller 1403. The liquid vapour material ejected from the chamber 1501 may be used according to a number of methodologies. In one of these, the endoscope may be manoeuvred to a location where medicament is to be dispensed at a particular location. Liquid may then be input into the chamber 1501 (or may already be so inserted) by opening inlet valve 1502 and then a heater unit 1503 energised to raise the temperature and pressure of the liquid medicament. The medicament can then be dispensed when the pressure and/or temperature reaches a predetermined value ejecting vaporised medicament and liquid medicament at a desired location. As with all of the above-described embodiments, the ejection cycle may be repeated many times if desired.

As an alternative, the liquid and liquid vapour ejected material can be used to clear a blockage in arteries and/or veins or the like. In this sense certain embodiments can be used in the bloodstream at blockages (such as in restricted blood flow disease due to furring of the arteries). In this case a water based or other neutral solution ejected by the above-mentioned techniques may be applied longitudinally along the line of a blocked vein/artery to thereby unblock the blockage. This is in addition to or replaces the present methodology which uses an expanding tube/balloon to clear the offending passage.

According to the embodiment shown in FIG. 13, a camera operated by a doctor is attached to a nano vapour explosion device and used to put a drug in exactly the right spot where a malfunction has taken place. Certain embodiments are not restricted to intestinal use but rather could be used also in a respiratory system of the main tracheal tubes and in the blood environment may have applications in the cardiovascular system.

Although the embodiments described with respect to FIGS. 13 to 15 have been described relating to the use of endoscope-like devices, embodiments of the present invention are not so restricted. Rather, certain embodiments can be used to deliver drugs at the desired locations by introducing a device in the form of a pill-like device which then moves on its own, for example through the bloodstream or the intestinal track and which is tracked by X-ray machinery with a dye and a scanning system so that an operator sees on the screen where the device has got to. A wireless signal may be then transmitted to the device in the human body when a doctor determines that the device is at a desired location. The device would then eject drug or merely liquid to either deliver medicament or open a blocked passage at a desired location.

Figure 16:
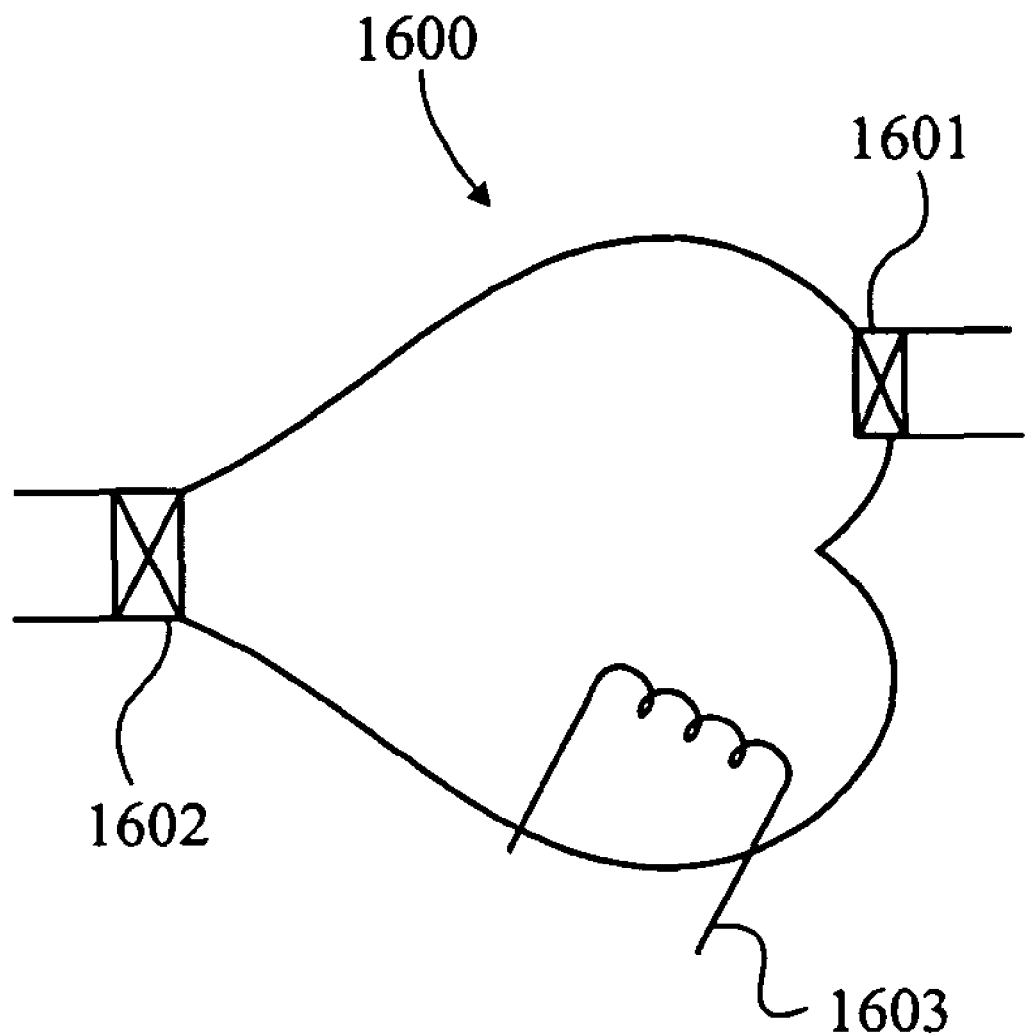
FIG. 16 illustrates how the chambers of the various described embodiments may be shaped.

FIG. 16 illustrates a liquid and liquid vapour explosion chamber 1600 which may be utilised according to any of the above-described embodiments. It will be understood that embodiments of the present invention are not restricted to use with substantially cylindrical shaped ejection chambers. Rather, unusual shapes or spherical shapes or, as in the case of FIG. 16, heart-shaped chambers having an inlet valve 1601, exit valve 1602 and heater element 1603 may be utilised.

Certain embodiments disclosed herein provide fundamental core technology relating to the use of an ejection chamber which ejects target matter via a vapour explosion process. By ejecting material via an explosive process the distance traversed by the spray of liquid and liquid vapour is greatly increased relative to known ejection systems. Also ejection occurs very rapidly in the order of tens of microseconds.

In particular embodiments, pressure in a chamber is increased by heating liquid in it. The liquid expands due to thermal expansion and therefore provides a higher pressure. Heating is achieved by electrical heating element or by other means such as via heat exchangers transferring heat from a local heat source into the liquid. All of the embodiments described above can be modified so that instead of heating liquid in an ejection chamber, pre-heated liquid is supplied at an inlet to the chamber under high pressure. Pressure would be built up in the chamber by continuing to pump pre-heated liquid into the chamber. This could be achieved via an external pump able to pump at high pressure. At some predetermined pressure value above a pressure into which ejected material is to be ejected, the inlet valve would be closed and an exit valve opened. The instantaneous reduction in pressure would be calculated to instigate a vaporization process of the liquid by virtue of its elevated temperature with respect to its boiling temperature. Liquid and vapour would thus literally explode from the exit valve of the chamber.

In the case of using water as a working liquid, velocities of up to 20 meters per second from a chamber just under 1 mm in size with a chamber pressure of 1.1 bar and injecting into ambient pressure (1.0 bar) can be achieved. In the case of a hydrocarbon liquid fuel being used, velocities of up to 100 meters per second can be achieved from a chamber about 2 cms in size and under a pressure of 10 bar injecting into a combustion chamber at 6 bar (in other words a 1 bar pressure difference between the ejection chamber and an adjacent combustion chamber).

Inlet and exit valves can be electronically controlled based on the pressure in the various vessels which can be easily monitored/measured via one or more sensors such as pressure transducers. When a certain pressure in the vessel is reached, the exit valve will open and when it falls below a second certain value the valve is closed. For the inlet valve this can either be opened and closed when certain higher limit and lower limit pressures are reached in the chamber or could open and close in a reverse fashion with respect to the exit valve. That is to say, when the exit valve is opened the inlet valve would be controlled to close and when the exit valve closes the inlet valve would open.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. Apparatus for ejecting material, comprising:
an ejection chamber arranged to hold and seal therein a portion of a selected liquid;
an inlet valve arranged to selectively fully open to thereby transfer liquid into the ejection chamber and then fully close to seal the portion of liquid in the ejection chamber; and
an exit valve arranged to selectively open to eject part or all of the portion of liquid material from said ejection chamber through the exit valve and then through a neck region as liquid vapour and/or liquid when at least one parameter associated with said ejection chamber satisfies a predetermined condition, the neck region being narrower in cross-sectional diameter than the ejection chamber such that the liquid vapour and/or liquid are ejected via a vapour explosion process when the exit valve opens; wherein
said exit valve is arranged to open when a temperature of the liquid in the ejection chamber is above a boiling point temperature associated with said liquid at a downstream position from the exit valve.

2. The apparatus as claimed in claim 1, further comprising:
a heater element disposed in or proximate to said ejection chamber and arranged to heat liquid in said ejection chamber.

3. The apparatus as claimed in claim 1, further comprising:
a pump member disposed in or proximate to said ejection chamber and arranged to raise a pressure in said ejection chamber.

4. The apparatus as claimed in claim 1, wherein:
said exit valve is arranged to selectively open when a pressure within the ejection chamber, said pressure comprising said predetermined parameter, is raised to a predetermined threshold value indicating satisfaction of said predetermined condition.

5. The apparatus as claimed in claim 1, wherein:
said inlet valve is arranged to selectively open to allow liquid to be introduced into the ejection chamber subsequent to material from the chamber previously being ejected via opening of the exit valve.

6. The apparatus as claimed in claim 1, wherein:
said ejection chamber comprises a narrow neck region along which liquid vapour and/or liquid is ejected.

7. The apparatus as claimed in claim 1, wherein:
the selected liquid is water.

8. The apparatus as claimed in claim 1, wherein:
the selected liquid is a flammable liquid.

9. The apparatus as claimed in claim 8, wherein:
the liquid is kerosene or petrol.

10. The apparatus as claimed in claim 1, wherein:
the exit valve is arranged to open when a pressure in said ejection chamber is 1.1 bar.

11. The apparatus as claimed in claim 1, wherein:
the liquid in the ejection chamber is heated above boiling point of that liquid at atmospheric pressure prior to the exit valve being opened.

12. The apparatus as claimed in claim 1, wherein:
said chamber diameter is in the range of 1 mm to 1 m.

13. The apparatus as claimed in claim 1, wherein:
said chamber is spherical in shape.

14. The apparatus as claimed in claim 1, wherein:
said chamber is heart-shaped.

15. The apparatus as claimed in claim 14, wherein:
said exit valve is located at an apex region of said heart-shaped chamber.

16. The apparatus as claimed in claim 1, wherein:
said chamber is substantially cylindrical in shape.

17. The apparatus as claimed in claim 1, wherein the apparatus narrows in cross-section from the ejection chamber to the neck region.

18. Apparatus for ejecting material, comprising:
an ejection chamber arranged to hold and seal therein a portion of a selected liquid;
an inlet valve arranged to selectively fully open to thereby transfer liquid into the ejection chamber and then fully close to seal the portion of liquid in the ejection chamber; and
an exit valve arranged to selectively open to eject part or all of the portion of liquid material from said ejection chamber through the exit valve and then through a neck region as liquid vapour and/or liquid when at least one parameter associated with the ejection chamber satisfies a predetermined condition, the neck region being narrower in cross-sectional diameter than the ejection chamber such that the liquid vapour and/or liquid are ejected via a vapour explosion process when the exit valve opens; wherein
said exit valve is arranged to open when a temperature of the liquid in the ejection chamber is above a boiling point temperature associated with said liquid at a downstream position from the exit valve, and
the liquid in the ejection chamber is heated above the boiling point, associated with said liquid, prior to the exit valve being opened.

19. A method for ejecting material, comprising:
holding and sealing therein a portion of a selected liquid in an ejection chamber;
increasing at least one parameter of the liquid in the ejection chamber;
selectively fully opening an exit valve of the ejection chamber when the parameter associated with the ejection chamber satisfies a predetermined condition;
fully closing the exit valve to seal the portion of liquid in the ejection chamber; and
ejecting part or all of the portion of liquid as liquid vapour and/or liquid from the ejection chamber via the exit valve and through a neck region downstream of the exit valve when a temperature of the liquid in the ejection chamber is above a boiling point temperature associated with said liquid at a downstream position from the exit valve, the neck region being narrower in cross-sectional diameter than the ejection chamber such that the liquid vapour and/or liquid are ejected via a vapour explosion process when the exit valve opens.

20. The method as claimed in claim 19, further comprising:
heating liquid to thereby increase a temperature of liquid held in the ejection chamber via a heating element disposed in or proximate to the ejection chamber.

21. The method as claimed in claim 20, further comprising:
heating liquid in the ejection chamber prior to the step of opening the exit valve.

22. The method as claimed in claim 19, further comprising:
increasing pressure in the ejection chamber via a pump member disposed in or proximate to said ejection chamber.

23. The method as claimed in claim 19, further comprising:
determining when the parameter satisfies said predetermined condition and opening the exit valve responsive to said determination.

24. The method as claimed in claim 19, further comprising:
introducing the portion of selected liquid into the chamber via an inlet valve.

25. The method as claimed in claim 24, further comprising subsequent to introducing the portion of selected liquid, selectively closing the inlet valve to thereby hold the portion of selected liquid in the ejection chamber.

26. The method as claimed in claim 19, further comprising:
subsequent to ejection of liquid vapour and/or liquid from the ejection chamber, selectively closing the exit valve.

27. The method as claimed in claim 19, further comprising:
preheating liquid supplied to the inlet valve prior to introduction into the ejection chamber.

28. The method as claimed in claim 19, further comprising:
monitoring pressure in the ejection chamber via at least one pressure sensor.

29. The method as claimed in claim 19, further comprising:
heating the liquid in the ejection chamber to a temperature above the boiling point temperature associated with said liquid at a pressure equal to a pressure of a gas located at a downstream position from the exit valve.

30. The method as claimed in claim 19, further comprising:
ejecting liquid vapour and/or liquid as a spray having a throw greater than 20.

31. The method as claimed in claim 19, further comprising:
ejecting liquid vapour and/or liquid as a spray having a throw greater than 100.

* * * * *